US00PP33081P2

(12) United States Plant Patent
Williams

(10) Patent No.: US PP33,081 P2
(45) Date of Patent: May 18, 2021

(54) ***COLOCASIA* PLANT NAMED 'TEA PARTY'**

(50) Latin Name: ***Colocasia* hybrid**
Varietal Denomination: Tea Party

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 0 days.

(21) Appl. No.: 16/873,515

(22) Filed: Apr. 24, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

(56) References Cited

PUBLICATIONS

*Colocasia* Tea Party, briansbotanicals.net from Pinterest, downloaded from https://www.pinterest.co.uk/pin/409264684887280515, downloaded Sep. 15, 2020, dated Jan. 2019, p. 1.*
*Colocasia* Tea Party PPAF—Brian's Botanicals Online Store and Blog, briansbotanicals.net/product/colocasia-tea-party-ppaf/, downloaded Sep. 15, 2020, dated Jan. 2019, p. 1.*

* cited by examiner

*Primary Examiner* — Anne Marie Grunberg
(74) *Attorney, Agent, or Firm* — Penny J. Aguirre

(57) ABSTRACT

A new cultivar of *Colocasia* plant named 'Tea Party' that is characterized by its smaller plant habit reaching 76 cm to 91 cm in height, its foliage that is dark to black in color with a reflective sheen, its leaves with a cup-like aspect, its petioles that are red to pink in color, and its clumping growth habit.

2 Drawing Sheets

Botanical classification: *Colocasia* hybrid.
Cultivar designation: 'Tea Party'.

BACKGROUND OF THE INVENTION

The present invention, *Colocasia* 'Tea Party', relates to a new and distinct interspecific hybrid of *Colocasia*, hereinafter referred to by its cultivar name, 'Tea Party'. 'Tea Party' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants with colorful leaves with cupped leaf habits with possible improved cold hardiness. 'Tea Party' arose from a cross made in June of 2007 between *Colocasia esculenta* 'Bikini-tini' (not patented) as the female parent and an unnamed and unpatented plant of *Colocasia* of hybrid origin as the male parent. 'Tea Party' was selected as a single unique plant in August of 2018 from amongst the seedlings derived from the above cross.

Asexual propagation of the new cultivar was first accomplished by root cuttings under the direction of the Inventor in Louisville, Ky. in August of 2018. Asexual propagation by root cuttings and tissue culture using meristematic tissue has determined that the characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Tea Party' as a new and unique cultivar of *Colocasia*.

1. 'Tea Party' exhibits a smaller plant habit reaching 76 cm to 91 cm in height.
2. 'Tea Party' exhibits foliage that is dark to black in color with a reflective sheen.
3. 'Tea Party' exhibits leaves with a cup-like aspect.
4. 'Tea Party' exhibits petioles that are red to pink in color.
5. 'Tea Party' exhibits a clumping growth habit.

The female parent of 'Tea Party' differs from 'Tea Party' in having a much taller plant height, foliage that is dark green in color with a matted texture, and dark maroon petioles. The male parent of 'Tea Party' differs from 'Tea Party' in having leaves that are flat in aspect, a taller plant height, in produces runners lacking a clump-forming growth habit. 'Tea Party' can be most closely compared to the *Colocasia* cultivars 'Black Sapphire' (U.S. Plant Pat. No. 27,966) and 'Black Ripple' (U.S. Plant Pat. No. 26,151). Both are similar to 'Tea Party' in having foliage that is dark in color with a reflective sheen and clumping growth habits. 'Black Sapphire' differs from 'Tea Party' in having a taller plant height, leaves that lacks a cup-like aspect, and dark purple grey petioles. 'Black Ripple' differs from 'Tea Party' in having a taller plant height, leaves that lack a cup-like aspect, and dark purple petioles.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Brian's Botanicals, Plants Nouveau, Grow Joy, AG 3, Evergreens turn-it tropical, Johnson Nursery Corporation, Walmart, Amazon, Michigan Bulb Company, Florida Hill Nursery, and Ken' s Nursery.

BRIEF DESCRIPTION OF THE DRAWINGS

The accompanying colored photographs illustrate the overall appearance and distinct characteristics of the new *Colocasia*, 'Tea Party' . The photographs were taken of a 1-year-old plant of 'Tea Party' as grown outdoors in a 2-gallon container under 6 mm poly and natural lighting in Louisville, Ky.

Figure 1:
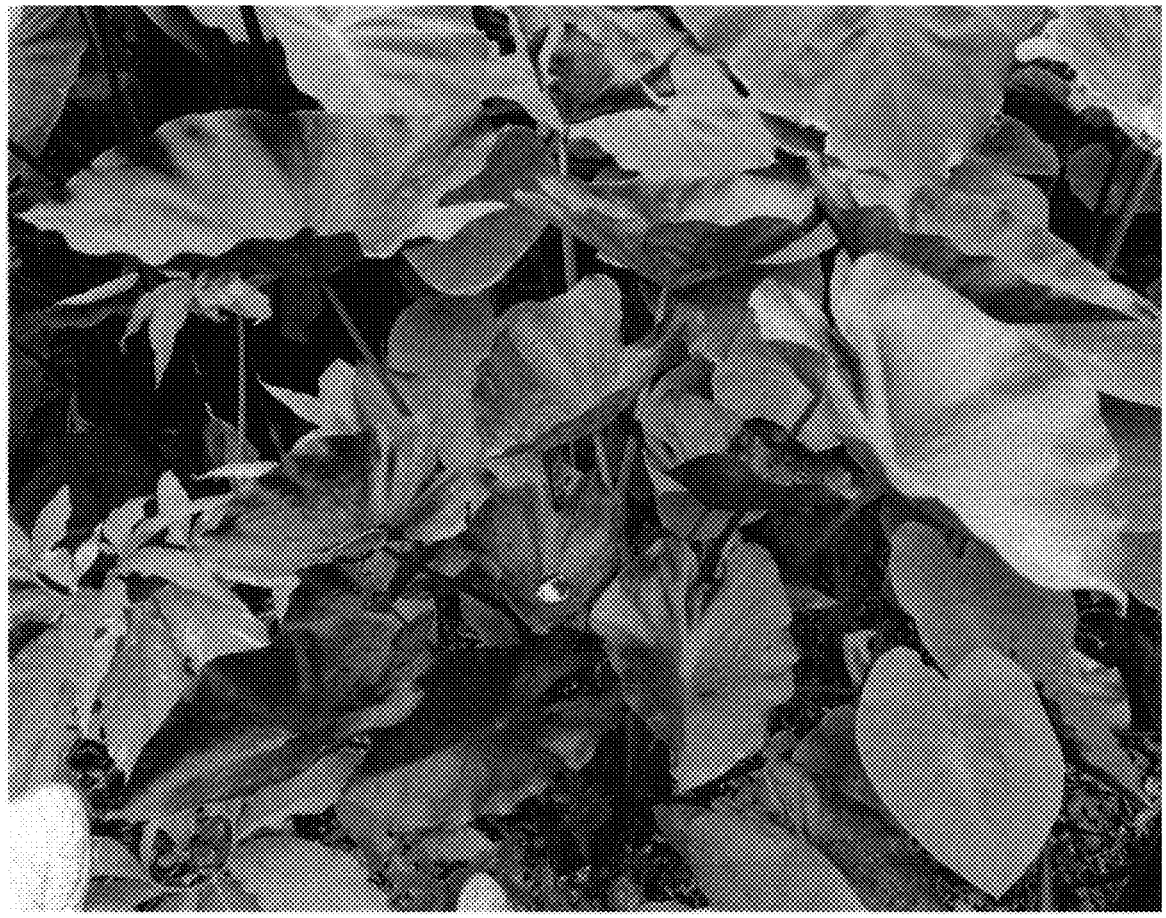
FIG. 1 provides a view of the plant habit of 'Tea Party'.
Figure 2:
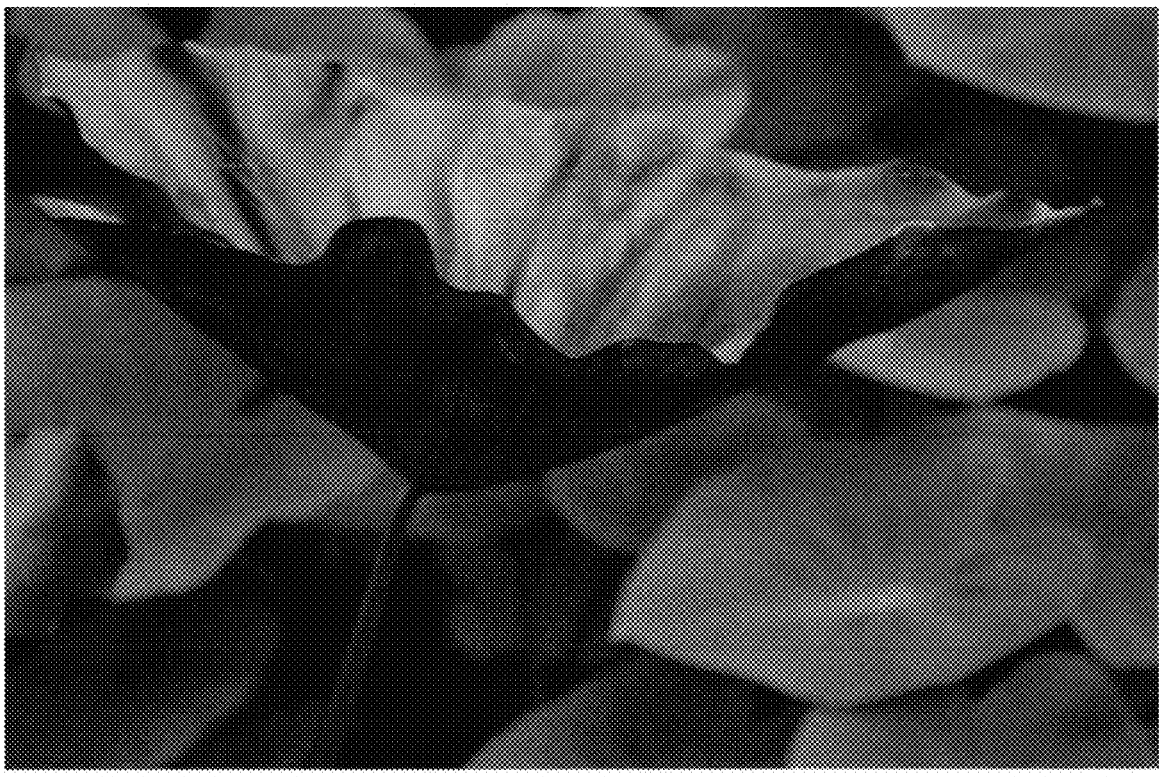

The photograph in FIG. 2 provides a close-up view of a leaf of 'Tea Party'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of two-year-old plants of the new cultivar as grown outdoors in full sun under 2 mm poly greenhouse plastic in two-gallon containers in Louisville, Ky. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms periodically year around depending on temperatures in Louisville, Ky.

*Plant type.*—Tropical perennial herb.

*Plant habit.*—Upright, stemless.

*Height and spread.*—Reaches 76 cm to 91 cm in height and spread as grown in a 2-gallon container.

*Hardiness.*—U.S.D.A. Zones 7 to 10.

*Diseases and pests.*—No susceptibility or resistance to diseases or pests has been observed.

*Roots.*—Fleshy with fibrous secondary roots, 159A in color.

*Corm.*—One per rhizome observed; an average of 2 cm in length and 1.5 cm in width, comprised of scales (about 40), surface is densely covered with long hair, roughly oval in shape, blend of 186A and 157A in color, cormels where not observed to form.

*Propagation type.*—Tissue culture.

*Growth rate.*—Vigorous.

*Time required for root development.*—An average of 3 to 5 weeks for root initiation with a rooted cutting produced between 3 to 6 weeks.

*Stem description.*—Rhizome-like trunk formed at the base of the petioles with age (see petiole description).

Foliage description:

*Leaf shape.*—Cordate, cupped upward.

*Leaf division.*—Single.

*Leaf base.*—Cuneate.

*Leaf apex.*—Rounded with cuspidate tip.

*Leaf venation.*—Pinnate, color: young leaves upper and lower surface match leaf surface, maturing leaves upper surface; 187A, maturing leaves lower surface; 185A, fully mature upper and lower surface; 200A, lower surfaces raised.

*Leaf margins.*—Slightly undulate, entire.

*Leaf attachment.*—Petiolate.

*Leaf arrangement.*—Emerge basally with petioles conduplicate.

*Leaf surface.*—Both surfaces matte and glabrous.

*Leaf orientation.*—Held primarily upright to petiole, cupped upward.

*Leaf color.*—Young leaves; upper surface a blend of 144A and 137A, lower surface a blend of 138A, maturing leaves; upper and lower surface 144A and blending with 185A and 183A, fully mature leaves; upper surface 200A, lower surface 200A and 187A.

*Leaf size.*—An average of 10 cm in length and 6.5 cm in width.

*Leaf sinus.*—An average of 1.5 cm in depth and width.

*Petioles.*—Held erect to semi-erect, an average of 38 cm in length, 1 cm in diameter, glabrous, glossy surface, color; young a blend of 196A, 187A, maturing and fully mature a blend of 185A and 187A.

Inflorescence description:

*Inflorescence type.*—Spadix surrounded by a spathe, male portion held above female portion, only female flowers are developed.

*Inflorescence size.*—An average of 14 cm in length and 2.5 cm in width.

*Inflorescence bud.*—Linear to slightly narrow lanceolate in shape, an average of 11 cm in length and 2 cm in width, color; a blend of 185A and 187A.

*Flower fragrance.*—Slight sweet fragrance.

*Lastingness of inflorescence.*—Inflorescence blooms intermittently during the bloom period, individual flowers last about 2 to 3 weeks.

*Inflorescence/flower quantity.*—An average of 110 female flowers sessile to spadix, sessile male flowers are undeveloped.

*Spathe.*—Hooded, bract, subtending spadix, an average of 14 cm in length and 3.5 cm in width, entire to slightly undulate margin, bottom portion; elliptic in shape, an average of 5 cm in length and 2.5 cm in width, apex fused to upper portion, truncate base, upper portion (hood); lanceolate in shape, an average of 10 cm in length and 4 cm in width, cuspidate apex, all surfaces coriaceous, glabrous, and smooth, upper and lower portion outer surface glaucescent, lower portion inner surface; dull and glabrous, color; upper portion outer and inner surface 10C, lower portion outer surface a blend of 83A, N82A and 18C and inner surface 2A and 1B.

*Spadix.*—Male portion; above female zone, upright linear in shape (phallus like), apex narrowly pointed, an average of 10 cm in length and 1 mm in width, N186A towards the top and 90A towards the base, female portion; conical in shape, an average of 2 cm in length and 1 cm in width, center color 18A, lower section color 140A and 140B.

*Peduncle.*—Grows from base of plant, oval in shape, an average of 14 cm in length and 1.5 cm in diameter, durable and strong, a blend of 103A, N186A and 187A in color, coriaceous, glabrous and smooth surface.

Reproductive organs:

*Gynoecium.*—1 pistil with sessile, discoid stigmas 8D in color, monocarpous ovary is round in shape, an average of 1.1 mm in length and width, and full of many minute ovules; oval in shape and translucent NN155C in color.

*Androecium.*—Undeveloped on plants observed, pollen was not observed but a low quantity of pollen has been observed on mature plants not available for data collection.

*Fruit and seed.*—None observed.

It is claimed:

1. A new and distinct cultivar of *Colocasia* plant named 'Tea Party' as herein illustrated and described.

* * * * *